(12) United States Patent
Boatman et al.

(10) Patent No.: US 6,409,752 B1
(45) Date of Patent: *Jun. 25, 2002

(54) FLEXIBLE STENT HAVING A PATTERN FORMED FROM A SHEET OF MATERIAL

(75) Inventors: Scott E. Boatman, Bloomington; Kimberly D. Brummett, Springville, both of IN (US)

(73) Assignee: Cook Incorporated, Bloomington, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/748,669

(22) Filed: Nov. 13, 1996

Related U.S. Application Data

(63) Continuation of application No. 08/378,073, filed on Jan. 25, 1995, now Pat. No. 5,632,771, which is a continuation of application No. 08/097,392, filed on Jul. 23, 1993, now abandoned.

(51) Int. Cl.[7] .................................................. A61F 2/06
(52) U.S. Cl. ...................................... 623/1.15; 623/1.34
(58) Field of Search ............................... 606/198, 191; 623/1.34, 1.15; 604/362, 103.1

(56) References Cited

U.S. PATENT DOCUMENTS

| | | | |
|---|---|---|---|
| 3,868,956 A | 3/1975 | Alfidi et al. ................ 128/345 |
| 4,323,071 A | 4/1982 | Simpson et al. ............ 128/343 |
| 4,332,254 A | 6/1982 | Lundquist ................... 128/344 |
| 4,345,602 A | * 8/1982 | Yoshimura et al. |
| 4,439,185 A | 3/1984 | Lundquist .................... 604/97 |
| 4,468,224 A | 8/1984 | Enzmann et al. ........... 604/247 |
| 4,512,338 A | 4/1985 | Balko et al. ................ 128/1 R |
| 4,516,972 A | 5/1985 | Samson ....................... 604/282 |
| 4,538,622 A | 9/1985 | Samson et al. ............. 128/772 |
| 4,553,545 A | 11/1985 | Maass et al. ................ 606/198 |
| 4,554,929 A | 11/1985 | Samson et al. ............. 128/772 |
| 4,569,347 A | 2/1986 | Frisbie ......................... 128/344 |
| 4,571,240 A | 2/1986 | Samson et al. ............... 604/96 |
| 4,572,186 A | 2/1986 | Gould et al. ................ 128/341 |
| 4,616,652 A | 10/1986 | Simpson ...................... 128/344 |
| 4,655,771 A | 4/1987 | Wallsten ......................... 623/1 |
| 4,680,031 A | 7/1987 | Alonso ............................ 623/2 |
| 4,681,110 A | * 7/1987 | Wiktor |

(List continued on next page.)

FOREIGN PATENT DOCUMENTS

| | | | |
|---|---|---|---|
| EP | 0364787 | * | 4/1990 |
| EP | 0481365 | | 4/1992 |
| EP | 0540290 | | 5/1993 |
| FR | 2617721 | | 1/1989 |
| FR | 2660562 | | 10/1991 |
| SU | 660689 | | 5/1979 |
| WO | 9306792 | | 4/1993 |

*Primary Examiner*—Michael H. Thaler
(74) *Attorney, Agent, or Firm*—Richard J. Godlewski

(57) ABSTRACT

A flexible stent having a waveform pattern formed from a sheet of biocompatible material and into a tubular shape for maintaining the patency of a lumen such as in a coronary vessel. The waveform pattern of the stent is formed from a flat sheet of malleable, biocompatible material by, for example, photochemically etching the sheet and leaving a framework or plurality of closed cells. The waveform pattern is formed into a tubular shape around a deflated, delivery catheter balloon with segments of the closed cells being interposed only overlapping a reinforcing member extending longitudinally along the stent. The stent material is treated to reduce the coefficient of friction of the material and to aid in the radial expansion of the stent with the balloon. Radiopaque markers are positioned at the ends of the stent to aid the physician in positioning the stent at an occlusion site.

23 Claims, 9 Drawing Sheets

U.S. PATENT DOCUMENTS

| | | | | |
|---|---|---|---|---|
| 4,693,721 A | | 9/1987 | Ducheyne | 623/16 |
| 4,723,549 A | | 2/1988 | Wholey et al. | 128/344 |
| 4,733,665 A | | 3/1988 | Palmaz | 128/343 |
| 4,739,762 A | | 4/1988 | Palmaz | 128/343 |
| 4,748,982 A | | 6/1988 | Horzewski et al. | 128/344 |
| 4,748,986 A | | 6/1988 | Morrison et al. | 128/772 |
| 4,762,128 A | | 8/1988 | Rosenbluth | 128/343 |
| 4,790,315 A | | 12/1988 | Mueller, Jr. et al. | 128/344 |
| 4,800,882 A | | 1/1989 | Gianturco | 128/303 R |
| 4,812,120 A | | 3/1989 | Flanagan et al. | 433/173 |
| 4,848,342 A | | 7/1989 | Kaltenbach | 128/341 |
| 4,877,030 A | * | 10/1989 | Beck et al. | |
| 4,892,541 A | | 1/1990 | Alonso | 623/2 |
| 4,893,623 A | | 1/1990 | Rosenbluth | 606/192 |
| 4,907,336 A | | 3/1990 | Gianturco | 29/515 |
| 4,969,458 A | | 11/1990 | Wiktor | |
| 5,007,926 A | | 4/1991 | Derbyshire | 623/1 |
| 5,019,090 A | | 5/1991 | Pinchuk | 606/194 |
| 5,030,233 A | | 7/1991 | Ducheyne | 623/16 |
| 5,041,126 A | | 8/1991 | Gianturco | 606/195 |
| 5,059,211 A | | 10/1991 | Stack et al. | 606/198 |
| 5,100,429 A | | 3/1992 | Sinofsky et al. | 606/195 |
| 5,102,417 A | * | 4/1992 | Palmaz | 606/195 |
| 5,104,404 A | * | 4/1992 | Wolff | 623/1 |
| 5,108,416 A | | 4/1992 | Ryan et al. | 606/194 |
| 5,129,910 A | * | 7/1992 | Phan et al. | 606/127 |
| 5,133,732 A | | 7/1992 | Wiktor | 623/1 X |
| 5,135,536 A | | 8/1992 | Hillstead | 623/1 X |
| 5,147,385 A | | 9/1992 | Beck et al. | 623/1 |
| 5,158,548 A | | 10/1992 | Lau et al. | 604/96 |
| 5,161,547 A | | 11/1992 | Tower | 606/198 X |
| 5,192,307 A | | 3/1993 | Wall | 606/198 X |
| 5,354,309 A | | 10/1994 | Schnepp-Pesch et al. | 606/198 |
| 5,370,691 A | * | 12/1994 | Samson | 623/12 |
| 5,383,926 A | * | 1/1995 | Lock et al. | 606/198 X |
| 5,423,849 A | * | 6/1995 | Engelson et al. | 606/191 |
| 5,599,291 A | * | 2/1997 | Balbierz et al. | 604/264 X |

\* cited by examiner

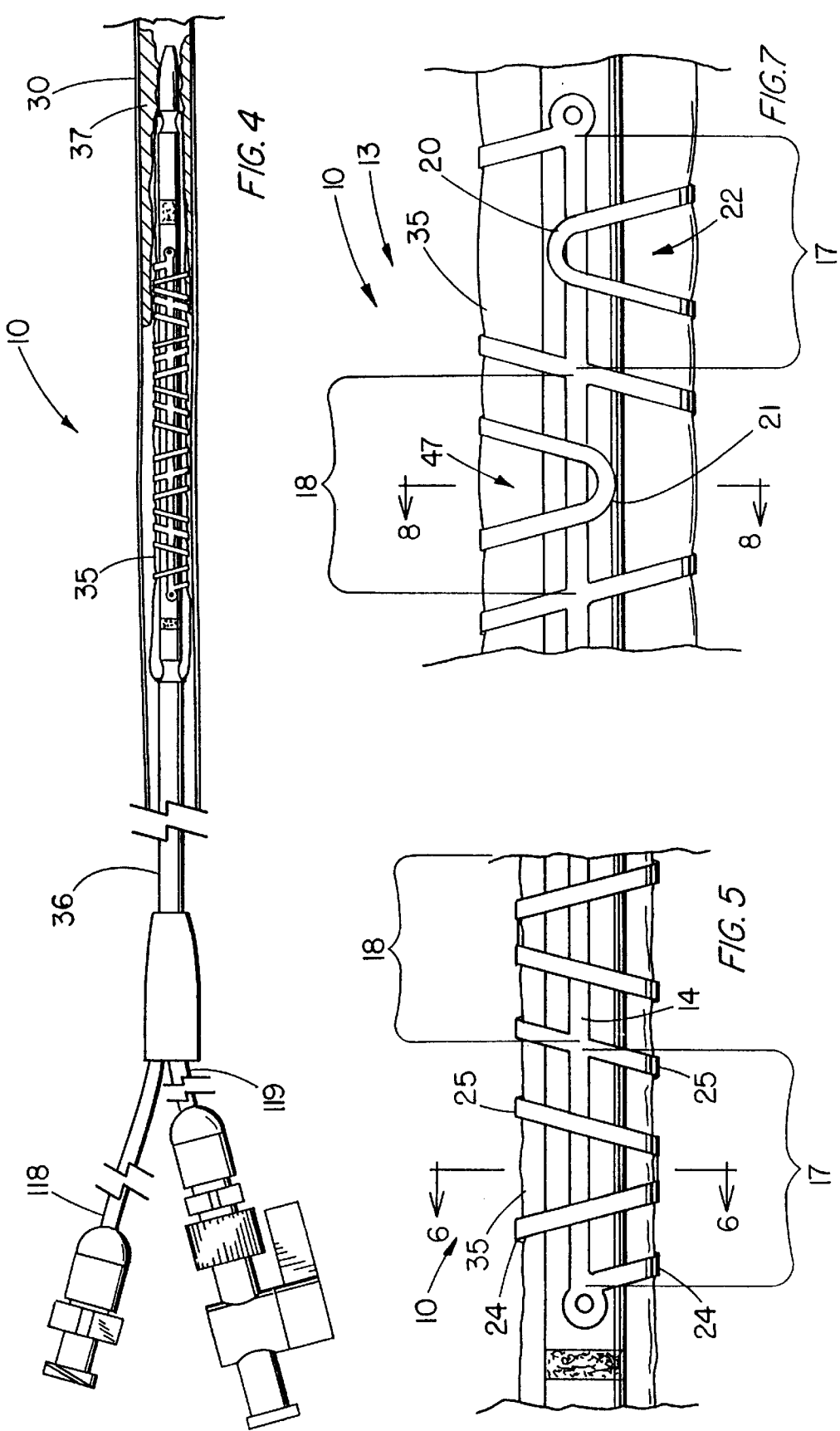

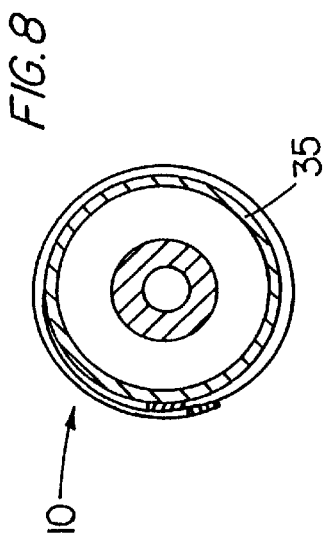
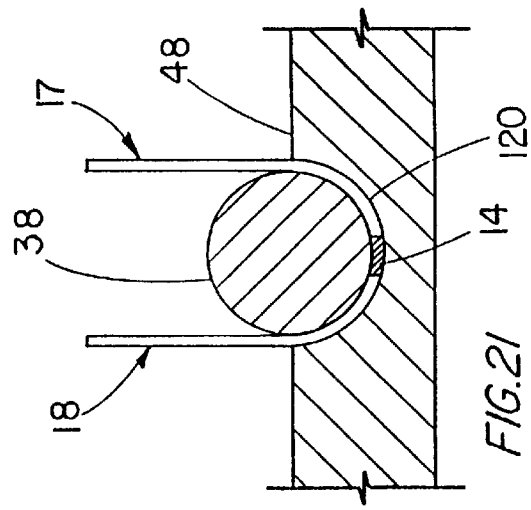
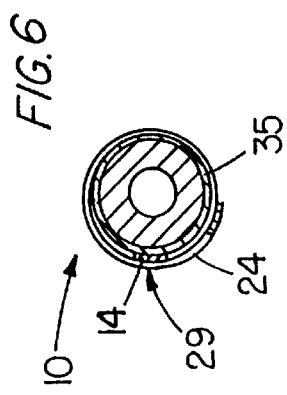
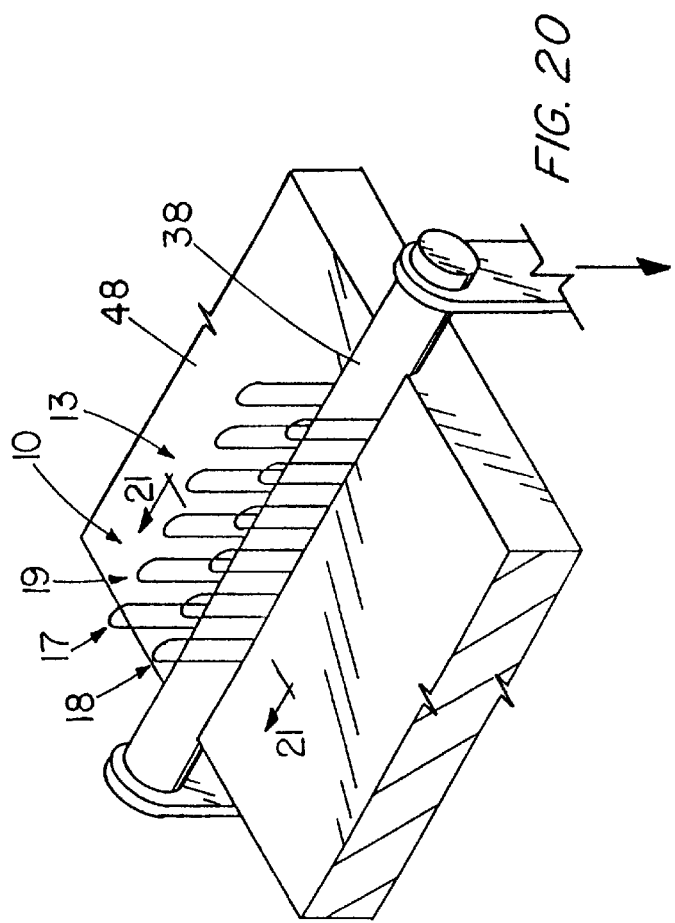

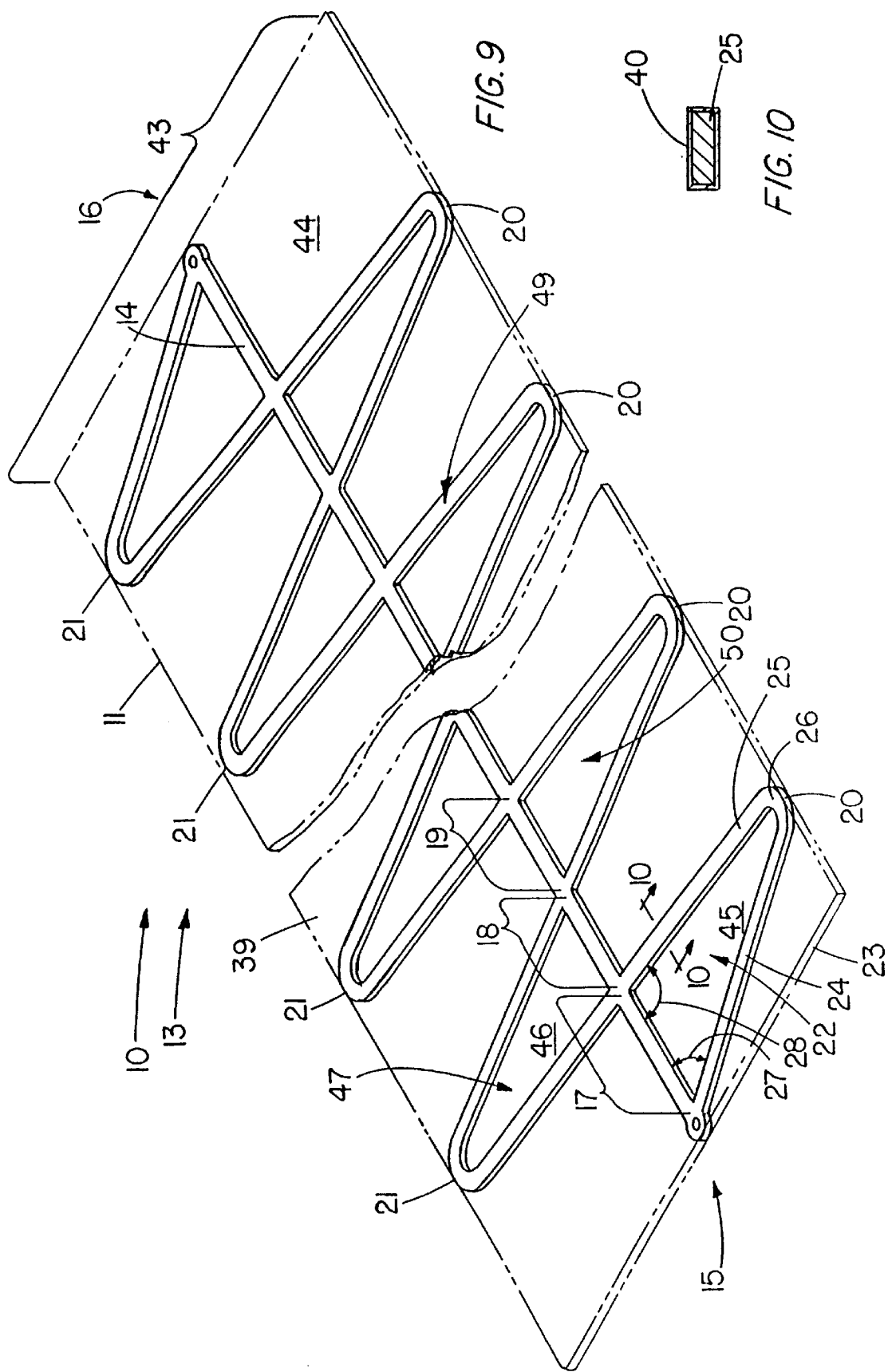

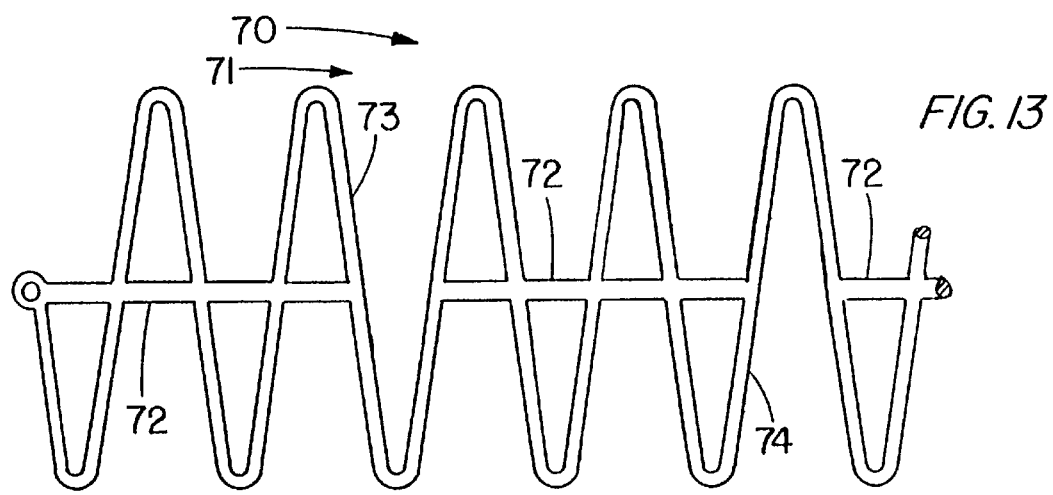
FIG. 13
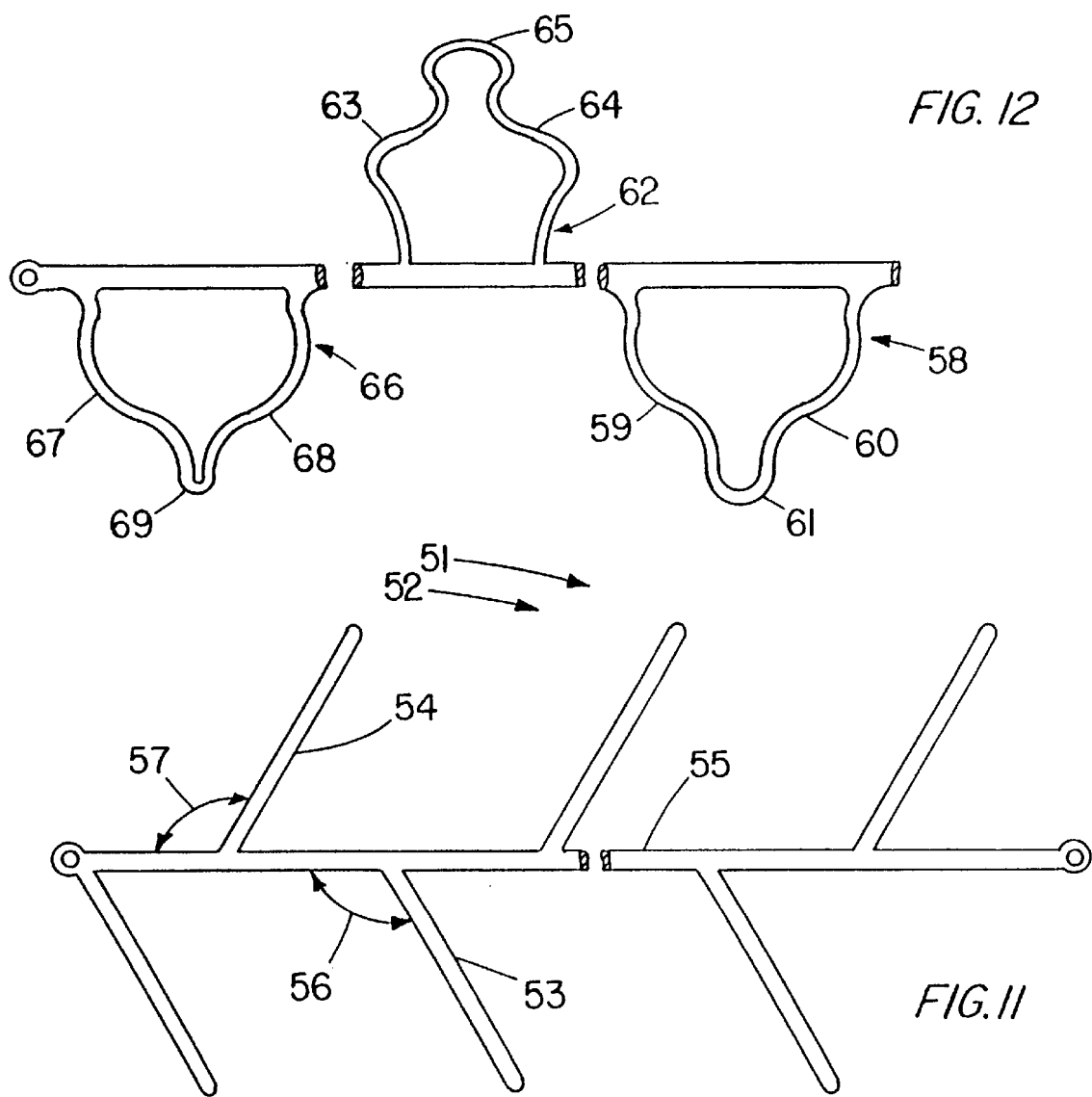
FIG. 12
FIG. 11

FLEXIBLE STENT HAVING A PATTERN FORMED FROM A SHEET OF MATERIAL

This is a continuation Ser. No. 08/378,073 filed on Jan. 25, 1995 now U.S. Pat. No. 5,632,771 which is a file wrapper continuation of Ser. No. 08/097,392 filed on Jul. 23, 1993, now abandoned.

TECHNICAL FIELD

This invention relates generally to balloon expandable stents and, in particular, to a flexible stent having a waveform pattern formed from a sheet of biocompatible material and into a cylindrical surface or tubular shape.

BACKGROUND OF THE INVENTION

Vascular stents are deployed at a narrowed site in a blood vessel of a patient for widening the vessel lumen and circumferentially supporting the vessel wall. Vascular stents desirably present a small cross-sectional dimension or profile for introducing the stent into the affected vessel lumen.

One approach to providing a vascular stent is the use of a piece of wire bent into a number of turns. Although suitable for its intended use, a problem with these bent wire stents is that stress points are formed at each wire bend or turn. As a result, the wire stent is structurally compromised at a number of points. Furthermore, bent wire stents lack longitudinal stability. For example, a wire stent is typically positioned in a blood vessel over an inflatable balloon. The balloon expands first at opposite ends, where the balloon is not in contact with the wire stent. As a result, the wire stent is longitudinally compressed between the inflated balloon ends. With continued inflation, the middle of the balloon expands, thereby unevenly expanding the wire bends of the longitudinally compressed wire stent. In an attempt to remedy the problem, the stent wire material has been formed to cross over or attach to itself. A problem with this attempted remedy is that the cross-sectional dimension of the stent, or stent profile, is increased, and the stent intrudes into the effective lumen of the blood vessel. The effective lumen of the blood vessel is further constricted by the growth of endothelial tissue layers over the stent wire. As a result, the stent and tissue growth impede fluid flow and cause turbulence in the vessel lumen. Another problem with this attempted remedy is that galvanic action, exposure to a reactive surface, or ion migration, occurs at the wire-to-wire contact points. The wire stent material rubs when movement occurs during ordinary blood flow and pulsation as well as patient muscle movement.

Another approach to providing a vascular stent is the use of a piece of metal cannula with a number of openings formed in the circumference thereof. A problem with the use of a metal cannula stent is that the stent is rigid and inflexible. As a result, the stent is difficult, if not impossible, to introduce through the tortuous vessels of the vascular system for deployment at a narrowed site. Furthermore, the stent is too rigid to conform with a curvature of a blood vessel when deployed at an occlusion site. Another problem with the use of a metal cannula stent is that the stent longitudinally shrinks during radial expansion. As a result, the position of the metal cannula stent shifts, and the stent supports a shorter portion of the blood vessel wall than anticipated merely by stent length.

Yet another approach to providing a vascular stent is the use of a wire mesh that is rolled into a generally tubular shape. A problem with the use of a wire mesh stent is that the overlapping wires forming the mesh increase the stent profile, thereby reducing the effective lumen of the blood vessel. The growth of endothelial tissue layers over the wire mesh further reduces the effective blood vessel lumen. Another problem with this approach is that ion migration also occurs at the wire-to-wire contact points.

Still yet another approach to providing a vascular stent is the use of a flat metal sheet with a number of openings formed in rows therein. The flat metal sheet stent also includes three rows of fingers or projections positioned on one edge of the stent along the axis thereof. When expanded, a row of the fingers or projections is positioned through a row of openings on the opposite edge is of the stent for locking the expanded configuration of the stent. A problem with the use of the flat metal sheet stent is that the overlapping edges of the stent increase the stent profile. Again, the stent profile and endothelial growth reduce the effective blood vessel lumen. Another problem with the use of the flat metal sheet stent is that the fingers or projections along one edge of the stent make wire-to-wire contact with the opposite edge of the stent. As a result, the metal edges of the stent rub during movement caused by blood flow, pulsation, and muscle movement. Yet another problem with the use of the flat metal sheet stent is that the fingers or projections extend radially outwardly and into the vessel wall. As a result, the intimal layer of the vessel wall is scraped, punctured, or otherwise injured. Injury and trauma to the intimal layer of the vessel wall result in hyperplasia and cell proliferation, which in turn effect stenosis or further narrowing of the vessel at the stent site.

SUMMARY OF THE INVENTION

The foregoing problems are solved and a technical advance is achieved in an illustrative embodiment of a flexible stent comprising a waveform pattern that is formed from a sheet of malleable, biocompatible material having a specified uniform thickness. The pattern is formed into a tubular shape and into an overlapping state around a delivery catheter balloon for introduction through tortuous vessels to, for example, an occlusion site in a coronary vessel. To provide longitudinal flexibility while preventing longitudinal contraction or expansion of the stent during radial expansion of the stent, the pattern advantageously includes a reinforcing member extending longitudinally therealong. A plurality of cells extends laterally from the reinforcing member with selected of the closed cells each having a fixedly sized aperture therein. The closed cells are interposed when the stent is in the tubular shape. To minimize the thickness of the stent and the growth of endothelial cells therearound, each segment of the cells extends laterally from the reinforcing member and does not overlap itself or any adjacent laterally extending segment of the cells. The sheet of biocompatible material with the pattern formed therein is formed into a radially alterable tubular shape around a delivery catheter balloon for introduction to the occlusion site. The balloon radially expands the stent to engage the vessel wall surface and to maintain the vessel lumen in an open condition. The expanded stent in a nonoverlapping state advantageously has a minimal thickness for endothelial tissue to form thereover. As a result, the vessel lumen is advantageously maintained with the largest diameter possible.

The pattern of the stent when in the tubular shape includes an overlapping state in which at least one segment of the selected cells overlaps the reinforcing member and forms a combined thickness with and along the reinforcing member of no more than substantially twice the thickness of the sheet of material. A deflated, delivery catheter balloon is positioned within the tubular-shaped stent to radially expand the stent to a nonoverlapping, expanded state when positioned at the occlusion site. The outermost longitudinal edges of the tubular stent move radially and circumferentially relative to each other when the stent is being radially altered. These outermost edges advantageously engage the surface of the lumen wall to maintain the stent in the expanded state. These outermost edges are most evident on the curved end segments of the interposed cells of the pattern when in the tubular shape. To aid expansion of the stent with the delivery balloon, the stent surface material is treated to lower its coefficient of friction. In one instance, the treatment comprises a coating of parylene on the surface of the sheet of material. Other coating materials include polytetrafluoroethylene. Furthermore, the surface of the stent may be ion beam bombarded to advantageously change the surface energy density and the coefficient of friction.

To maintain the moment of inertia or stiffness of the stent, each segment of the cells has a width substantially greater than the specified thickness of the sheet material. Increasing the width of the laterally extending segments also increases the surface area of the stent and support of the vessel wall.

To increase the expansion ratio of the stent, the laterally extending cells may be formed around the reinforcing member more than once and within the aperture of a closed cell without each segment overlapping itself or any adjacent cell segment. The width of the cell along the reinforcing member is advantageously selected so that each laterally extending segment forms a predetermined angle so as not to overlap itself or any adjacent cell segment. This is to advantageously maintain a combined thickness with and along the reinforcing member of no more than substantially twice the thickness of the sheet of material.

Radiopaque markers are advantageously positioned at one or more ends of the waveform pattern to aid the physician in positioning the stent at the occlusion site.

The method of making the balloon expandable stent includes the steps of providing a sheet of malleable material having an initial surface area and removing a majority of the material so that the sheet becomes a framework of integrated support members having a small surface area relative to the initial surface area of the sheet of material.. The method also includes positioning the framework around a cylindrical mandrel so that the framework defines at least a partially cylindrical surface or tubular shape. The removing step also includes removing isolated portions of the sheet so that the framework includes a plurality of closed cells bounded by the integrated support members. The removing step is also carried out so that the framework has a fixed length despite a reduction or expansion of the radius of the cylindrical surface or tubular shape. The cylindrical surface or tubular shape has a longitudinal axis and a substantially circular cross-section. The removing step is carried out so that the cylindrical surface or tubular shape is sufficiently flexible about the longitudinal axis to adapt the stent to curved passages within a body vessel without significantly altering the circular cross-section.

The stent of the present invention may also be characterized as a sheet of malleable material which has had a portion of the material removed so that the sheet becomes a framework of integrated support members arranged around a longitudinal axis to define a cylindrical surface. The cylindrical surface has a reduced diameter for delivery of the stent into a passage within a body vessel. The cylindrical surface is also plastically expandable from the reduced diameter to an expanded diameter for holding the passage open. The cylindrical surface has a range of diameters between the reduced diameter and the expanded diameter that are free from overlapping material. Each of the support members of the stent has a width and a thickness significantly less than the width. The support members are integrated in a way that the framework maintains a fixed length when the cylindrical surface is expanded from the reduced to the expanded diameter. One of the support members is a reinforcing member that extends from a first to a second end of the stent. The remaining support members extend laterally on each side of the reinforcing member. The cylindrical surface of the stent also defines a cylindrical surface when expanded to the expanded diameter. In addition, the cylindrical surface is sufficiently flexible about the longitudinal axis so that the stent can advantageously adapt to curved passages within a body vessel without significantly altering its circular cross section. The framework of the stent also includes a plurality of closed cells bounded on all sides by the integrated support members.

BRIEF DESCRIPTION OF THE DRAWING

FIG. 4 depicts a partially sectioned, longitudinal view of the stent of FIG. 1 in an overlapping state positioned about a delivery catheter balloon and introduced to an occlusion site;

FIG. 5 depicts an enlarged, partial view of the stent of FIG. 4 in an overlapping state;

FIG. 6 depicts a cross-sectional view of the stent of FIG. 5 taken along the line 6—6;

FIG. 7 depicts an enlarged, partial view of the stent of FIG. 4 in a partially expanded state;

FIG. 8 depicts a cross-sectional view of the stent of FIG. 7 taken along the line 8—8;

FIG. 9 depicts a partially sectioned, pictorial view of the stent of FIG. 1 in a flat configuration as formed from a sheet of malleable material;

FIG. 10 depicts a cross-sectional view of a segment of the stent of FIG. 9 taken along the line 10—10;

FIGS. 11–19 depict alternative embodiments of the stent of the present invention with different waveform patterns formed in a sheet of material; and FIGS. 20 and 21 depict the method of forming the stent of FIG. 1 into a tubular shape and around a delivery catheter balloon.

DETAILED DESCRIPTION

Figure 1:
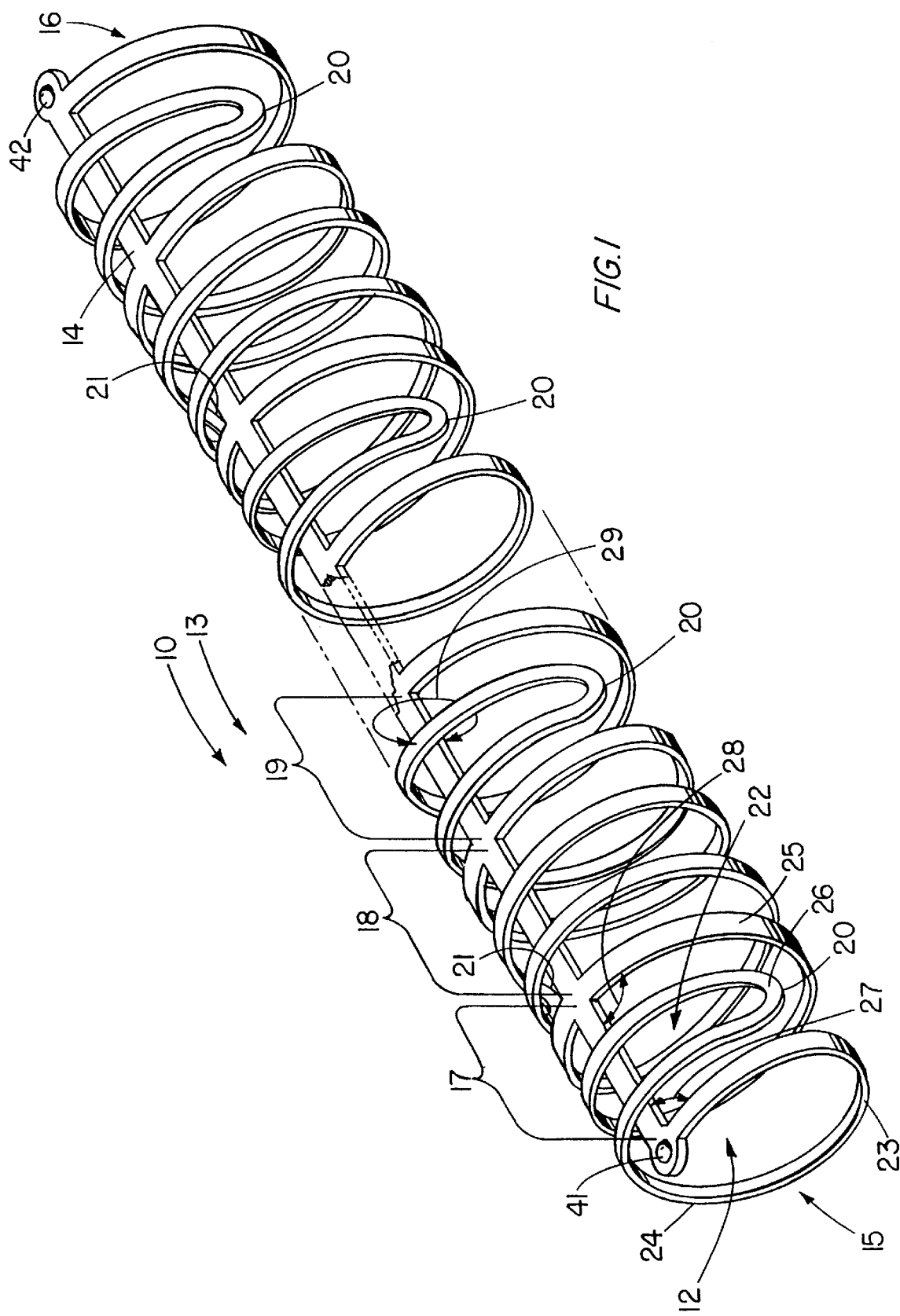
FIG. 1 depicts a pictorial view of the preferred illustrative embodiment of an unmounted flexible stent of the present invention having a waveform pattern formed from a sheet of material into a tubular shape and an overlapping state.

FIG. 1 depicts a pictorial view of a preferred illustrative embodiment of unmounted flexible stent 10 in an overlapping state and comprising a waveform pattern 13 formed from a flat sheet of biocompatible material and into a tubular shape 12. The tubular shaped pattern is expanded with a delivery catheter balloon in a body passage such as a blood vessel to maintain an open lumen therethrough. As depicted in FIG. 9, pattern 13 is formed from a flat sheet 11 of malleable, biocompatible material such as stainless steel by, for example, photochemically removing a majority of the sheet material and leaving a framework of integrated support members that has a small surface area relative to the initial surface area of the sheet. After formation from the sheet, the pattern is formed into a partially cylindrical or U-shaped surface around a cylindrical mandrel and then positioned in the overlapping state around a deflated, delivery catheter balloon and into tubular shape 12.

Pattern 13 includes a reinforcing member 14 extending longitudinally between opposite ends 15 and 16 for providing longitudinal stability thereof, particularly during radial expansion of the stent in the body passage. The length of prior art stents that are formed from a tube typically shorten as the stent is radially expanded. When formed into a tubular shape, pattern 13 includes a plurality of interposed closed cells 17–19 that extend laterally from the reinforcing member for providing vessel wall support. The tubular shaped pattern also exhibits longitudinal flexibility for introducing the stent through tortuous vessels to, for example, a coronary artery. Unlike a wire stent in which a wire is bent into a waveform pattern, waveform pattern 13 is formed from a flat sheet of material without any stresses being introduced at the curved segments thereof. As a result, thickness 23 of stent 10, as well as sheet 11, can be made extremely thin in comparison to that of a wire stent to minimize endothelial tissue buildup in the vessel. The same well-known moment of inertia or stiffness of a wire stent is maintained by adjusting the width of each pattern member segment for a given sheet thickness.

When stent 10 is positioned in the overlapping state around a deflated catheter balloon, any segment of a laterally extending cell that overlaps the reinforcing member only forms a combined thickness 29 with and along the reinforcing member of no more than substantially twice the thickness of the sheet material. Accordingly, the stent is formed with an extremely small outside diameter while maximizing the inside diameter of the stent for receiving the delivery catheter balloon. When the stent is expanded in a blood vessel, the tubular shape is radially altered from a reduced, minimal inside diameter to an expanded diameter for holding the blood vessel open. In addition, oppositely facing, outermost longitudinal edges 20 and 21 of the pattern move radially and circumferentially relative to each other so that the pattern in the sheet of material is not stressed or deformed in the plane of the sheet of material. The substantially cylindrical surface of the tubular shape has a range of diameters between the expanded diameter and the reduced diameter for holding the vessel open in which the interposed cells are free of overlapping sheet material. The pattern is integrated in such a way that the framework thereof maintains a fixed length when the cylindrical surface of the tubular shape is expanded from the reduced diameter of the overlapping state to a larger diameter.

Interposed cell 17 includes fixedly sized aperture 22 with segments 24–26 and reinforcing member 14 disposed around the aperture. Substantially straight segments 24 and 25 extend laterally from reinforcing member 14, and curved segment 26 interconnects straight segments 24 and 25. Straight segments 24 and 25 are positioned circumferentially around the tubular shape in the space of aperture 22 without overlapping themselves or other adjacent cell segments for minimizing the stent profile or thickness in the overlapping state. Straight segments 24 and 25 extend laterally from the reinforcing member at angles 27 and 28, for example, both slightly acute at 82–83 degrees. Therefore, as depicted in FIG. 1, the straight segments cross over reinforcing member 14 but do not overlap themselves or each other. Furthermore, interposed cell 17 is separated from adjacent cells so that the segments of other cells do not overlap segments of cell 17. The width of the segments is greater than the thickness of the segments, or the sheet of biocompatible material, to maintain an acceptable moment of inertia and to increase the effective vessel wall support area. For example, segments 24–26 are approximately 0.014" wide and 0.005" thick.

Figure 2:
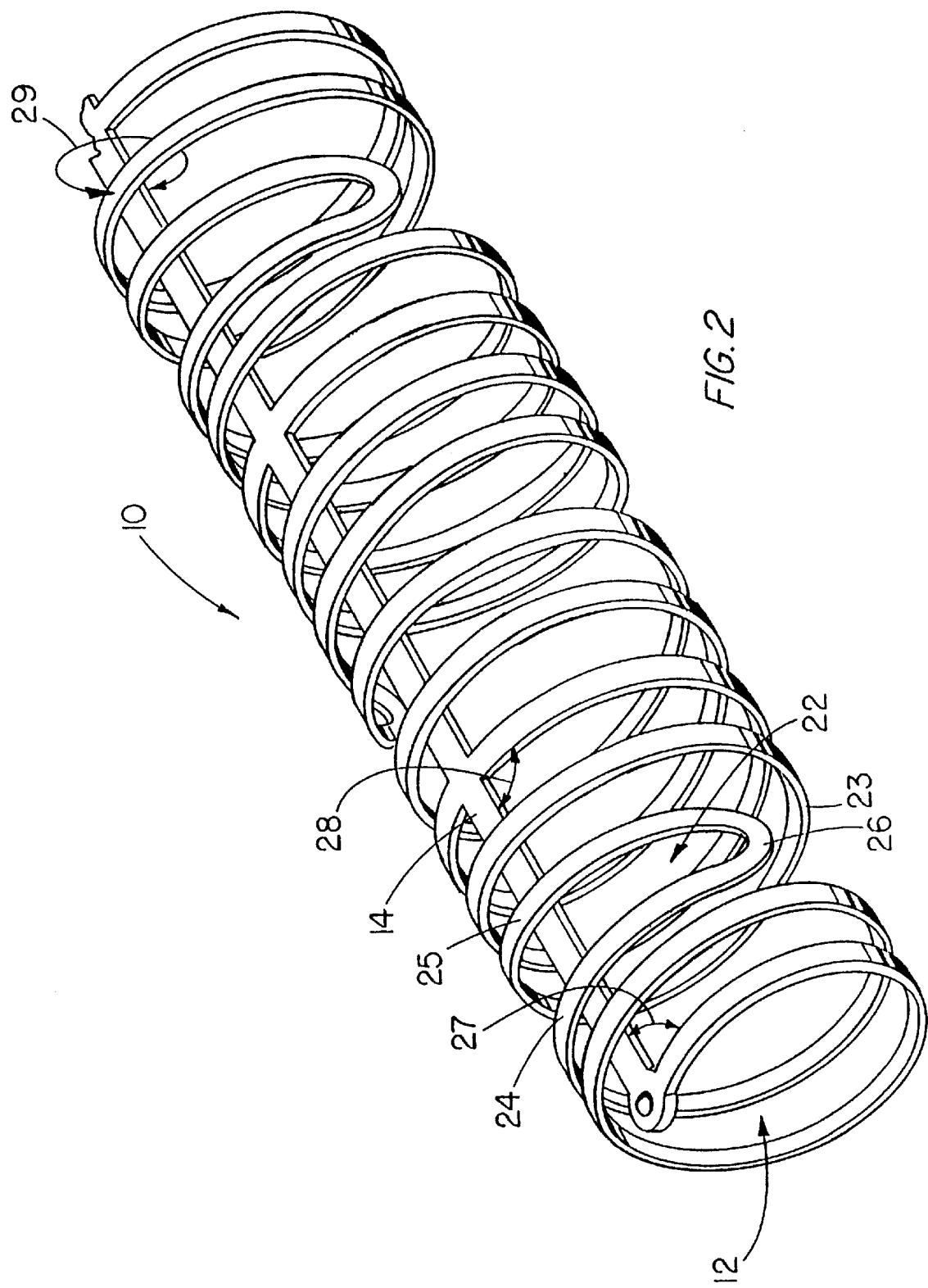
FIG. 2 depicts a pictorial view of another illustrative embodiment of an unmounted flexible stent of the present invention in an overlapping state with segments of the closed cells crossing over the reinforcing member of the stent more than once.

FIG. 2 depicts a pictorial view of another illustrative embodiment of stent 10 in an overlapping state with laterally extending segments 24–26 wrapped into tubular shape 12 and into the space of aperture 22. However, straight segments 24 and 25 cross over reinforcing member 14 at least two times in the overlapping state. Combined thickness 29 of the overlapping state stent with and along the reinforcing member is still no more than the thickness of straight segment 24 and reinforcing member 14, or no more than substantially twice the thickness of the sheet of biocompatible material. Although, straight segments 24 and 25 cross over the reinforcing member more than once, the segments do not overlap themselves or any segments of adjacent cells. The expansion ratio of stent 10 from being in an overlapping state with a reduced or minimal diameter to an expanded, nonoverlapping state with an expanded diameter for holding a body vessel open can be varied by appropriately selecting the width of the cell along the reinforcing member and the height or extension of the cell from the reinforcing member. After the desired moment of inertia is selected for straight segments 24 and 25, the width of each segment is calculated based on the thickness of the sheet material. With a desired expansion ratio, the reduced and expanded diameters along with the circumference of the expanded stent are calculated. From this, the number of times the straight segments must cross the reinforcing member is determined. The width and height of each cell is derived based on the width of each segment and the desired spacing to ensure that the segments do not overlap themselves or segments from adjacent cells. With this determination, angles 27 and 28 that segments 24 and 25 make with reinforcing member 14 will vary. On a more practical basis, the expanded and reduced diameters along with the sheet material thickness are more commonly selected to determine the remaining parameters of the cells.

Figure 3:
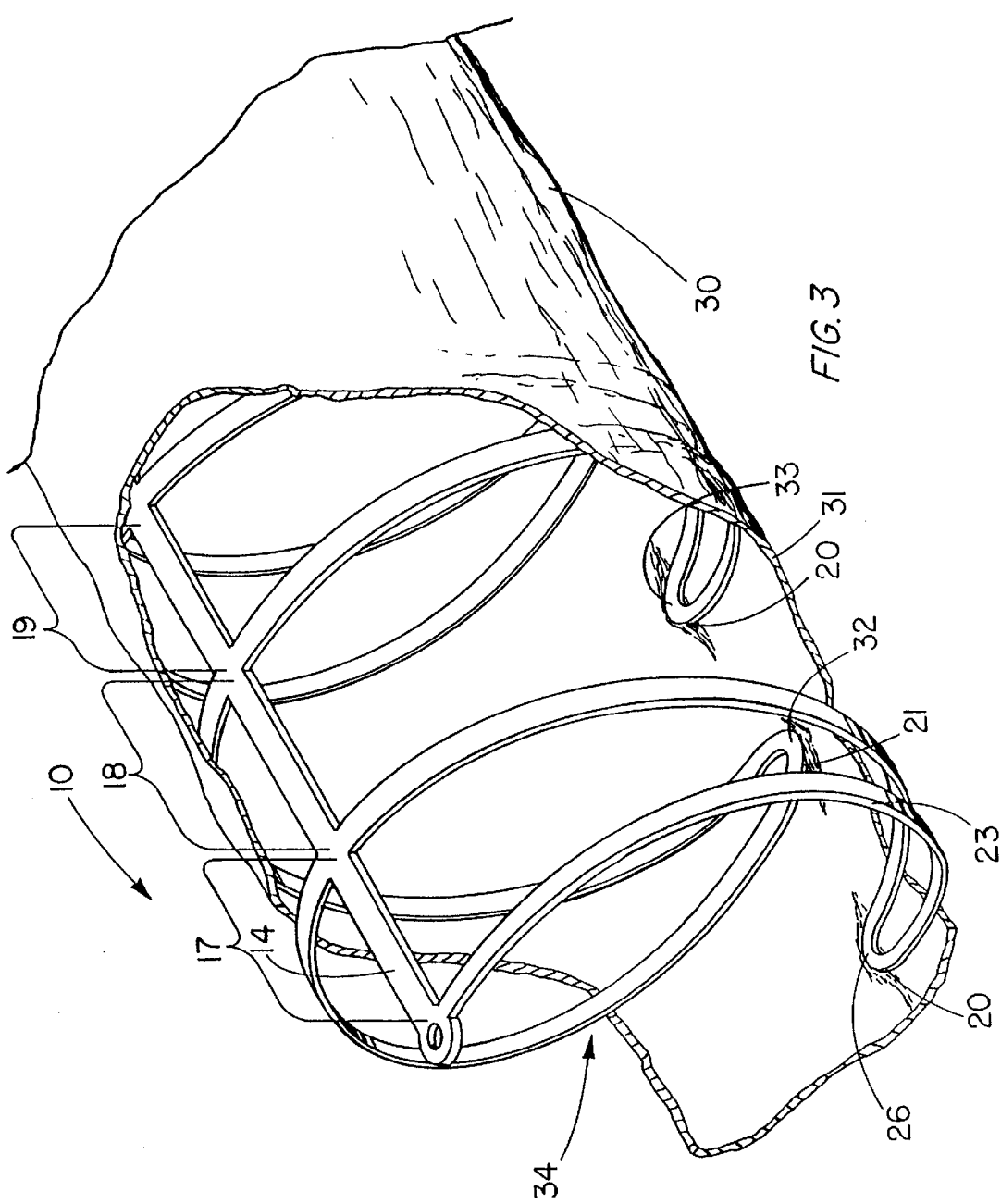
FIG. 3 depicts a pictorial view of the stent of FIG. 1 in an expanded, nonoverlapping state and positioned in a blood vessel.

FIG. 3 depicts a pictorial view of stent 10 of FIG. 1 positioned in blood vessel 30. The laterally extending segments of alternatingly interposed cells 17–19 support vessel wall 31. Cells 17–19 are interposed about respective curved segments 26, 32, and 33 thereof for providing an expanded tubular shape or a complete cylindrical surface 34. Upon inflation of the ballon of a balloon catheter, the stent is expanded with oppositely facing, outermost longitudinal edges 20 and 21 moving radially outward and circumferentially toward each other. Curved segments 26 and 33, each with edge 20, and interposed curved segment 32 with oppositely facing edge 21, also move radially, and circumferentially apart. However, the interposed cells are urged circumferentially together under the closing force of the vessel wall when the balloon is deflated. When the interposed cells move together, oppositely facing edges 20 and 21 of curved segments 26 and 33 and interposed curved segment 32 engage vessel wall 31 and securely lodge the stent in an expanded state.

FIG. 4 depicts a partially sectioned, longitudinal view of stent 10 of FIG. 1 in an overlapping state positioned about balloon 35 of delivery catheter 36 and introduced to a partially occluded region 37 of blood vessel 30. Well-known side arms 118 and 119 of catheter 36 are provided with lumens extending through the catheter for inserting the catheter over a wire guide and for inflating balloon 35.

FIG. 5 depicts an enlarged, partial view of stent 10 of FIG. 4 in an overlapping state with interposed cells 17 and 18 positioned about balloon 35. Straight segments 24 and 25 of cell 17 and the straight segments of cell 18 overlap reinforcing member 14.

FIG. 6 depicts a cross-sectional view of stent 10 of FIG. 5 positioned around delivery catheter balloon 35 taken along the line 6—6. The overlapping state stent has an outside diameter of approximately 0.055", and the deflated balloon has an outside diameter of approximately 0.039". Combined thickness 29 of segment 24 and member 14 is no more than substantially twice the thickness of the sheet material.

FIG. 7 depicts an enlarged, partial view of stent 10 of FIG. 4 in a partially expanded, but still overlapping state positioned about partially inflated balloon 35. Stent 10 has a 3 mm inside diameter when fully expanded, and balloon 35 has an outside diameter of approximately 3.5 mm when fully expanded. Pattern 13 with interposed cells 17 and 18 and respective fixedly sized apertures 22 and 47 remain stable while oppositely facing, outermost edges 20 and 21 move radially outward and circumferentially toward each other for expanding the tubular shape of the stent. Pattern 13 is not longitudinally shortened during positioning or expansion of the stent.

FIG. 8 depicts a cross-sectional view of stent 10 of FIG. 7 positioned around inflated delivery catheter balloon 35 taken along the line 8—8.

FIG. 9 depicts a partially sectioned, pictorial view of stent 10 of FIG. 1 in a flat configuration as formed from sheet 11 of malleable, biocompatible material 39. Biocompatible material 39 is preferably a commercially available, malleable material such as Series 316L (low carbon) stainless steel that is typically annealed for minimizing the tendency to recoil once the stent is expanded by an inflated balloon. Biocompatible material 39 commonly has a surface with a coefficient of friction capable of holding an unexpanded stent tightly around a balloon, thereby occasionally inhibiting the ability to expand the balloon and stent. Therefore, the biocompatible material of the stent preferably includes a surface treatment for lowering the coefficient of friction such as coating 40 formed of, for example, parylene material, as depicted in FIG. 10. Parylene material is a polymer used in coating pacemaker leads and is commercially available from Specialty Coating Systems of Union Carbide in Clear Lake, Wis. Coating 40 alternatively comprises polytetrafluoroethylene or another antithrombotic material. The surface and the surface energy density of the material can also be changed by ion beam bombardment, which is commercially available from the spire Corporation of Bedford, Mass.

Pattern 13 is formed from sheet 11 of biocompatible material by photochemically etching, stamping, laser cutting, or any other of a number of well-known methods. Forming pattern 13 in a thin sheet of material provides a stent with an increased vessel contact surface area without increasing the metal mass of the stent, which is a limitation of prior art wire stents. A stent with an expanded inside diameter of 3 mm, for example, is formed from a sheet of material approximately 0.371" wide, 0.7865" long, and 0.003" thick. Reinforcing member 14 and straight segments 24 and 25 are approximately 0.012" wide. Curved segment 26 has a 0.010" inside radius along oppositely facing, outermost edges 20 and 21. Reinforcing member 14 is positioned along the centerline of pattern 13 and has a .005" radius at intersections with the straight segments of the interposed cells. Centerlines through apertures 22 and 50 transverse to the reinforcing member are positioned 0.143" apart. Opposite stent ends 15 and 16 have a 0.017" radius formed thereon defining projections that extend therefrom to free ends to define the furthest extents of the unopposed proximal and distal ends of the stent, and the projections include openings (see FIG. 3) through the thickness of the sheet that define closed rings therearound or eyelets for positioning radiopaque markers 41 and 42 therein or fixedly attaching them thereto. Radiopaque markers 41 and 42 are affixed by placing a 0.010" diameter piece of radiopaque material such as gold, platinum, tungsten, or iridium in the eyelet and heating the material to melt it in place so that the material extends across the oepnings of the eyelets, as in FIG. 1. Alternatively, radiopaque markers are positioned in the eyelets by crimping or any other well-known fastening method.

FIG. 10 depicts a cross-sectional view of straight segment 25 of stent 10 of FIG. 9 taken along the line 10—10. Straight 25 segment has a rectangular cross-section and includes outer surface treatment 40 for decreasing the coefficient of friction on the stent surface. The coated segment is approximately 0.005" thick and 0.014" wide.

A method of making balloon expandable stent 10 includes providing a sheet 11 of material with an initial surface area 43 and removing a majority 44 of the sheet material so that the remaining sheet 49 becomes a framework of integrated support members such as waveform pattern 13 having a small surface area relative to the initial surface area. The method also includes positioning the framework around a cylindrical mandrel so that the framework defines a cylindrical surface 34 or tubular shape 12. The cylindrical surface has a radius that can be expanded or reduced; however, the length of the surface and stent remains fixed despite a reduction or expansion of the radius. Cylindrical surface 34 also has a longitudinal axis and a substantially circular cross section. The surface is sufficiently flexible about the longitudinal axis so that the stent can adapt to curved passages within a body vessel without significantly altering the circular cross section. By way of example, the material removed from sheet 11 to form stent 10 includes isolated portions 45 and 46 resulting in respective apertures 22 and 47 for providing respective closed cells 17 and 18, each bounded by integrated support members such as straight segments 24 and 25, interconnecting curved segment 26, and reinforcing member 14. The stent framework is formed into at least a partially cylindrical or U-shaped surface with, for examples cylindrical mandrel 38 and U-shaped form 48 as depicted in FIGS. 20 and 21. The stent is then formed into cylindrical surface 34 or tubular shape 12 around a delivery catheter balloon with the aid of form 48.

FIGS. 20 and 21 depict U-shaped form 48 as a flat plate having a straight U-shaped channel 120 formed therein. In the cross-sectional view of FIG. 21, it is seen that channel 120 has a U-shaped or semi-circular surface. After stent 10 is formed from a sheet of biocompatible material and into the framework or waveform pattern 13, the stent is placed flat upon the plate such that reinforcing member 14 is coincident with the center line of the channel. Stent 10 in its flat configuration is then pressed into U-shaped channel 120 and against the semi-circular surface with cylindrical mandrel 38. Closed interposed cells such as 17–19 extend out of the channel and away from the cylindrical mandrel as shown. The cylindrical mandrel is removed, and a delivery catheter balloon inserted in the U-shaped stent. The stent is then formed into cylindrical surface 34 or tubular shape 12 around the delivery catheter balloon with the aid of U-shaped form 48 forming the U-shaped interposed cells around the balloon and into the cylindrical surface or tubular shape. Well-known pulling tools with hooks at the ends thereof can be used to engage the interposed cells to pull the cells tightly around the delivery catheter balloon. These pulling tools are disclosed with a very similar forming method in U.S. Pat. No. 4,907,336 of Gianturco, which is incorporated by reference herein.

FIGS. 11–19 each depict a partial, longitudinal view of an alternative embodiment of the stent of the present invention in a flat configuration and with a different waveform pattern formed from a sheet of material.

FIG. 11 depicts stent 51 with herringbone pattern 52 formed therein. Substantially straight segments 53 and 54 extend laterally from reinforcing member 55 at angles 56 and 57, both approximately 82–83 degrees, so that when the stent assumes a tubular shape, the segments overlap only the reinforcing member.

FIG. 12 depicts closed cell 58 of another embodiment of the stent of the present invention with mirror image curved segments 59 and 60 interconnected by curved segment 61. In a different configuration, closed cell 62 with mirror image curved segments 63 and 64 are interconnected by bulbous curved segment 65. In yet another configuration, closed cell 66 with mirror image curved segments 67 and 68 are interconnected by acutely curved segment 69. A pattern of any one or more of these closed cells can be formed from a sheet of biocompatible material and interposed to provide a stent of the present invention wherein the segments of the cells overlap only the reinforcing member when the stent is in an unexpanded, overlapping state.

FIG. 13 depicts stent 70, which is still another embodiment of the present invention, including waveform pattern 71 with a discontinuous longitudinal reinforcing member 72. Pattern 71 provides increased longitudinal flexibility about segments 73 and 74, which are not bounded or closed by reinforcing member 72.

Figure 14:
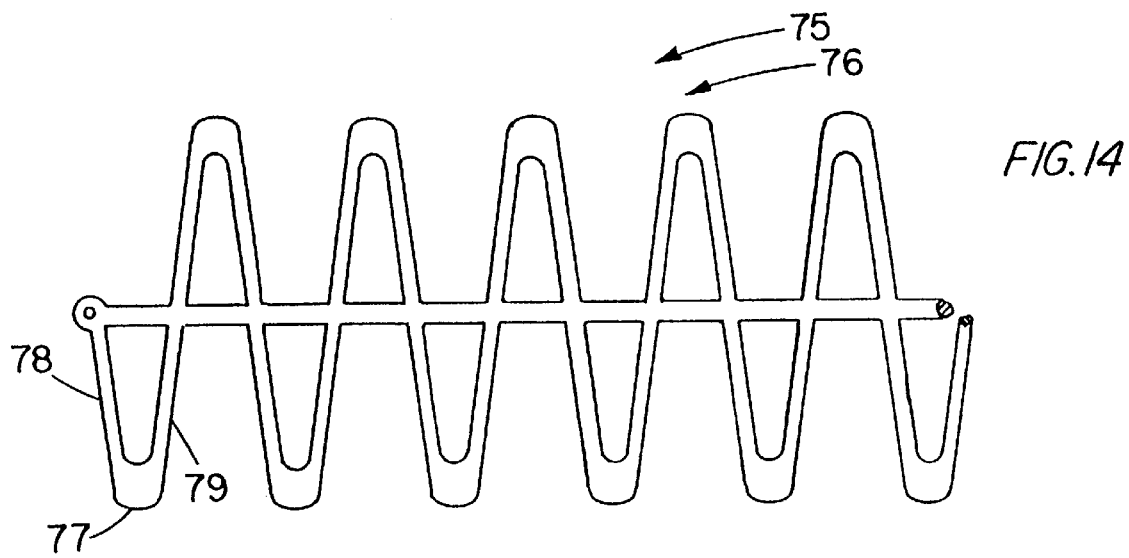

FIG. 14 depicts stent 75, which is yet another embodiment of the present invention, including waveform pattern 76 with curved segment 77 wider than straight segments 78 and 79. The additional width and surface area of the curved segments provide for increased support of a vessel wall.

Figure 15:
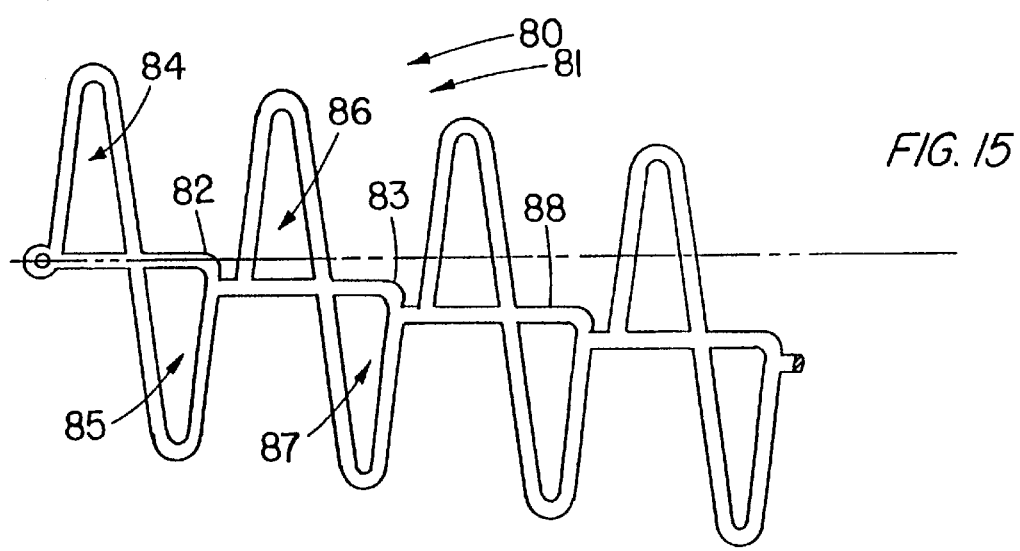

FIG. 15 depicts stent 80, which is still yet another embodiment of the present invention, with waveform pattern 81 including transverse steps 82 and 83 along the longitudinal axis of the stent. The transverse steps provide for uniform longitudinal flexibility around the circumference of the stent. The transverse steps are positioned after every pair of two interposed cells. Step 82 is positioned after cells 84 and 85, and step 83 is positioned after cells 86 and 87. Reinforcing member 88 extends longitudinally along the stent coincidentally with the transverse steps.

Figure 16:
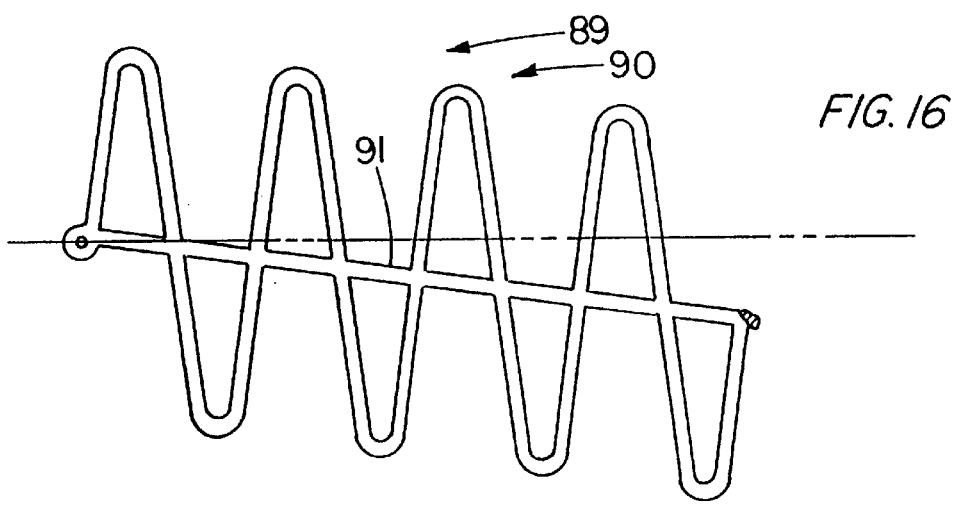

FIG. 16 depicts stent 89, which is another embodiment of the present invention, with waveform pattern 91 including reinforcing member 92 that is gradually angled with respect to the longitudinal axis of the stent. When stents 80 and 89 assume their expanded, tubular shapes, the interposed curved segments are positioned in a spiral about the circumference of the tubular shapes. This configuration also provides for more uniform longitudinal flexibility of the stent about the circumference of the stent.

Figure 17:
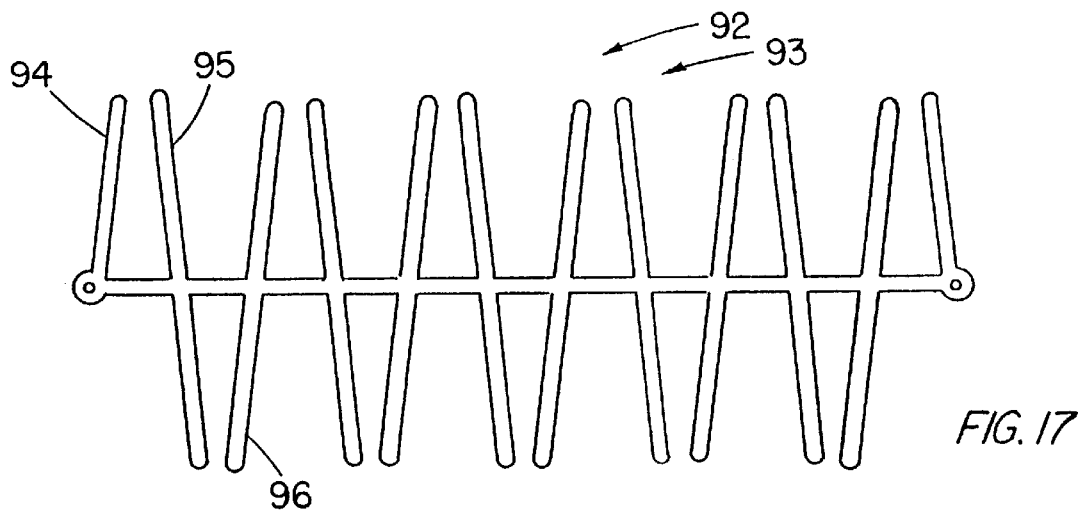

FIG. 17 depicts stent 92, which is yet another embodiment of the present invention, including pattern 93 without any curved segments interconnecting straight segments 94–96.

Figure 18:
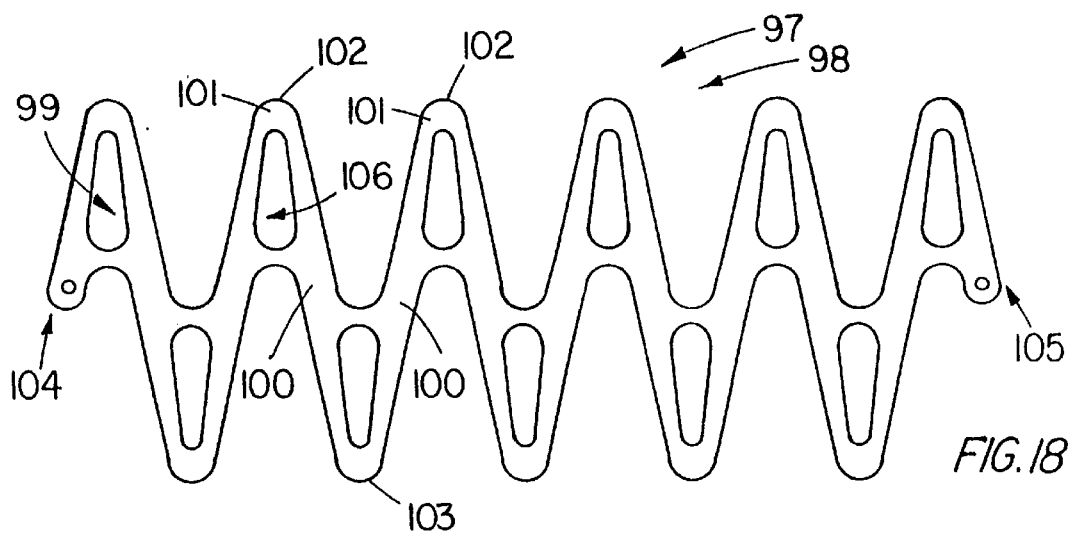

FIG. 18 depicts stent 97, which is still another embodiment of the present invention, with waveform pattern 98 including generally egg-shaped aperture such as 99 in a closed cell and reinforcing member 100 with a repeating curvature formed therein. Pattern 98 provides increased surface area for supporting a vessel wall. Stent 97 is formed of a sheet of biocompatible material approximately 0.372" wide, 0.955" long, and 0.003" thick. Curved segment 101 has a 0.021" radius along oppositely facing, outermost edges 102 and 103. Opposite stent ends 104 and 105 extend 0.0205" from the centerline of the stent, and each has a 0.041" radius formed thereon. Egg-shaped aperture 99 has approximately a 0.011" radius and a 0.020" radius with a length of 0.086" extending between the centers of the two radii and a length of 0.059" extending from the centerline of the stent and the center of the largest radius. A transverse centerline through aperture 99 is positioned 0.1658" from the transverse centerline through aperture 106.

Figure 19:
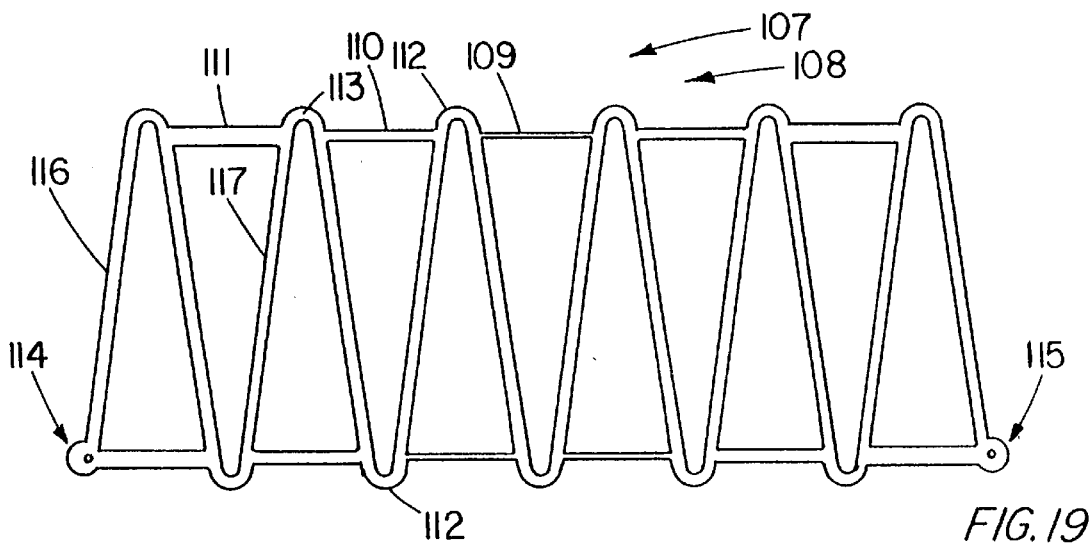

FIG. 19 depicts stent 107, which is still yet another embodiment of the present invention, with waveform pattern 108 including increasing width reinforcing members 109–111 positioned along oppositely facing, outermost stent edges 112. Stent 107 is formed of a sheet of biocompatible material approximately 0.381" wide, 1.026" long, and 0.003" thick. Curved segment 113 has a 0.010" radius along outermost edge 112. Reinforcing members 109–111 are positioned 0.033" from outermost edges 112 and have a 0.005" radius at intersections with the curved and straight segments. Opposite stent ends 114 and 115 have a 0.006" radius formed thereon. Segments 116 and 117 are approximately 0.012" wide. Reinforcing members 109–111 gradually increase in width from 0.006" at the center of the stent to 0.018" at the opposite ends.

It is to be understood that the above-described stent is merely an illustrative embodiment of the principles of this invention and that other stents may be devised by those skilled in the art without departing from the spirit and scope of this invention. It is contemplated that any overlapping state stent formed from a sheet of material to minimize endothelial tissue growth is within the spirit and scope of this invention. Any equivalent shape of the waveform as illustrated by the preferred and alternative embodiments of the stent is also contemplated.

What is claimed is:

1. A stent comprising:
   a member having opposite free ends and formed of a sheet of biocompatible material having a pattern in a surface of said sheet, said pattern including in said sheet a plurality of cells, said pattern further including an eyelet at at least one of said free ends of said member, said eyelet being of a fixed size smaller than a respective said cell, and wherein a radiopaque marker is positioned in said eyelet to clearly indicate a location of the at least one free end.

2. The stent of claim 1 wherein said radiopaque marker comprises a radiopaque material from a group consisting of at least one of gold, platinum, tungsten, or iridium.

3. The stent of claim 2 wherein said radiopaque material is melted into position in said eyelet and extends across an opening through said eyelet.

4. The stent of claim 2 wherein said radiopaque material is crimped into position in said eyelet and extends across an opening through said eyelet.

5. The stent of claim 1 further comprising a coating material over at least one of said sheet of biocompatible material and said radiopaque marker.

6. The stent of claim 5 wherein said coating material comprises at least of a group consisting of parylene, polytetrafluoroethylene, or an antithrombotic material.

7. The stent of claim 5 wherein said coating material has a coefficient of friction less than a coefficient of friction of at least one of said sheet of biocompatible material and said radiopaque marker.

8. The stent of claim 1 wherein at least one of said sheet of biocompatible material and said radiopaque marker has a predetermined surface energy density.

9. The stent of claim 1, wherein said sheet of biocompatible material includes a seamless sheet of biocompatible material.

10. The stent of claim 1, wherein said pattern further includes radiopaque markers at both said free ends of the stent.

11. The stent of claim 1, wherein said eyelet is a closed ring.

12. The stent of claim 1, wherein the eyelet is defined by an opening through a thickness of said sheet.

13. A tubular-shaped stent comprising:
a sheet of biocompatible material having a tubular shape and a pattern in a surface of said sheet, said pattern including a plurality of cells in said surface of said sheet;
said sheet includes an eyelet at at least one free end of said pattern that is defined by an opening through a thickness of said sheet, said eyelet being of a fixed size smaller than a respective said cell and
a radiopaque marker at said at least one free end of said sheet and positioned in said eyelet to clearly indicate a location of the at least one free end.

14. The tubular-shaped stent of claim 13 further comprising another radiopaque marker at an other of said free ends of said sheet.

15. The tubular-shaped stent of claim 13 wherein said radiopaque marker includes a radiopaque material.

16. The tubular-shaped stent of claim 15 wherein said radiopaque material comprises at least one of a group consisting of gold, platinum, tungsten, or iridium.

17. The tubular-shaped stent of claim 15 further comprising a coating material posited over said radiopaque material.

18. The tubular-shaped stent of claim 17 wherein said coating material comprises at least one of a group consisting of parylene, polytetrafluoroethylene, or an antithrombotic material.

19. The tubular-shaped stent of claim 13 wherein said radiopaque marker comprises gold melted into position in said eyelet and extends across an opening through said eyelet.

20. The tubular-shaped stent of claim 13 wherein said radiopaque marker comprises gold crimped into position into said eyelet and extends across an opening through said eyelet.

21. The tubular-shaped stent of claim 13, wherein said sheet of biocompatible material includes a seamless sheet of biocompatible material.

22. The tubular-shaped stent of claim 13, wherein said pattern further includes radiopaque markers at both said free ends of the stent.

23. The tubular-shaped stent of claim 13, wherein said eyelet is a closed ring.

* * * * *